United States Patent
Dowden et al.

(10) Patent No.: US 10,076,608 B2
(45) Date of Patent: Sep. 18, 2018

(54) METHOD AND APPARATUS FOR OVERLOAD PROTECTION IN MEDICAMENT SYRINGE PUMPS

(71) Applicant: Smiths Medical ASD, Inc., Plymouth, MN (US)

(72) Inventors: Taylor Dowden, Plymouth, MN (US); Jim Drost, Plymouth, MN (US); Grant Alan Adams, Plymouth, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days.

(21) Appl. No.: 15/327,948

(22) PCT Filed: Jul. 16, 2015

(86) PCT No.: PCT/US2015/040739
§ 371 (c)(1),
(2) Date: Jan. 20, 2017

(87) PCT Pub. No.: WO2016/014335
PCT Pub. Date: Jan. 28, 2016

(65) Prior Publication Data
US 2017/0203032 A1  Jul. 20, 2017

Related U.S. Application Data

(60) Provisional application No. 62/026,942, filed on Jul. 21, 2014.

(51) Int. Cl.
*A61M 5/168* (2006.01)
*A61M 5/145* (2006.01)

(52) U.S. Cl.
CPC ............ *A61M 5/168* (2013.01); *A61M 5/145* (2013.01); *A61M 2205/332* (2013.01)

(58) Field of Classification Search
CPC ................. A61M 5/168; A61M 5/145; A61M 2205/332; A61M 2205/3331;
(Continued)

(56) References Cited

U.S. PATENT DOCUMENTS 5,627,566 A * 5/1997 Litschel .................... B41J 5/10
345/168
6,485,465 B2  11/2002 Moberg et al.
(Continued)

FOREIGN PATENT DOCUMENTS

| GB | 2356349 A | 5/2001 |
|---|---|---|
| WO | WO 2013/177379 A1 | 11/2013 |
| WO | WO 2014/049647 A1 | 4/2014 |

OTHER PUBLICATIONS

International Preliminary Report on Patentability for corresponding International Application No. PCT/US2015/040739 dated Oct. 26, 2015; 5 pages.
(Continued)

*Primary Examiner* — Manuel Mendez
(74) *Attorney, Agent, or Firm* — Patterson Thuente Pedersen, P.A.

(57) ABSTRACT

An overload protection method and apparatus for a medicament syringe pump force sensor. A dome switch is employed with force sensor components of a medicament pump. The dome switch collapses at overload pressures, isolating the force sensor from pump driving forces that exceed the force sensor limit. An alarm signal can be triggered by the overload, and initiate pump shut down.

6 Claims, 7 Drawing Sheets

(58) Field of Classification Search
CPC .......... A61M 2205/50; A61M 2205/52; A61M 5/172; G06F 19/3468; G06F 21/32; G06F 3/0338; G06F 2203/04105; G06F 3/0414; A63F 13/218
USPC ................ 604/65–67, 151, 131; 128/DIG. 1, 128/DIG. 12, DIG. 13
See application file for complete search history.

(56) References Cited

U.S. PATENT DOCUMENTS

| | | | |
|---|---|---|---|
| 6,551,277 B1 | 4/2003 | Ford | |
| 6,800,069 B2 | 10/2004 | Lampropoulos et al. | |
| 7,041,082 B2 | 5/2006 | Blomquist et al. | |
| 7,442,186 B2 | 10/2008 | Blomquist | |
| 7,566,326 B2 | 7/2009 | Duchon et al. | |
| 7,635,349 B2 | 12/2009 | Tribe et al. | |
| 7,695,456 B2 | 4/2010 | Langley et al. | |
| 9,301,563 B2* | 4/2016 | Hardy ................ | A41D 19/0031 |
| 2003/0163089 A1 | 8/2003 | Bynum | |
| 2003/0229311 A1 | 12/2003 | Morris et al. | |
| 2005/0096593 A1 | 5/2005 | Pope et al. | |
| 2010/0089167 A1* | 4/2010 | Trieu .................. | A61M 5/1456 73/700 |
| 2013/0283934 A1 | 10/2013 | Bazargan et al. | |
| 2014/0188076 A1* | 7/2014 | Kamen ............... | A61M 5/1408 604/506 |
| 2015/0297832 A1 | 10/2015 | Blomquist | |
| 2016/0030676 A1 | 2/2016 | Bresina et al. | |
| 2016/0136353 A1 | 5/2016 | Adams | |

OTHER PUBLICATIONS

International Search Report for corresponding International Application No. PCT/US2015/040739 dated Oct. 26, 2015; 4 pages.
Written Opinion of the International Searching Authority for corresponding International Application No. PCT/US2015/040739 dated Oct. 26, 2015; 4 pages.
Search Report dated Feb. 16, 2018 for EP Application No. 15824397. 2, 7 pages.

* cited by examiner

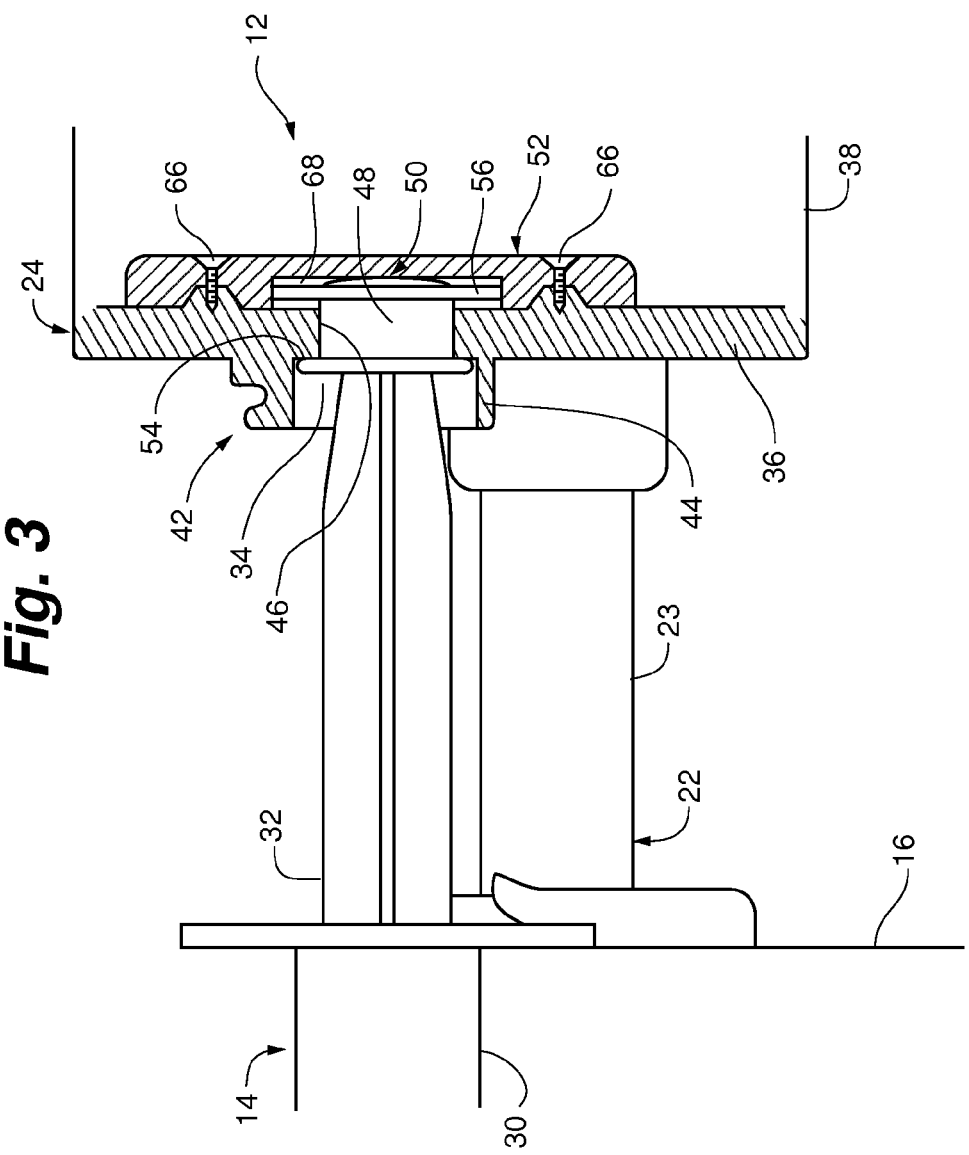

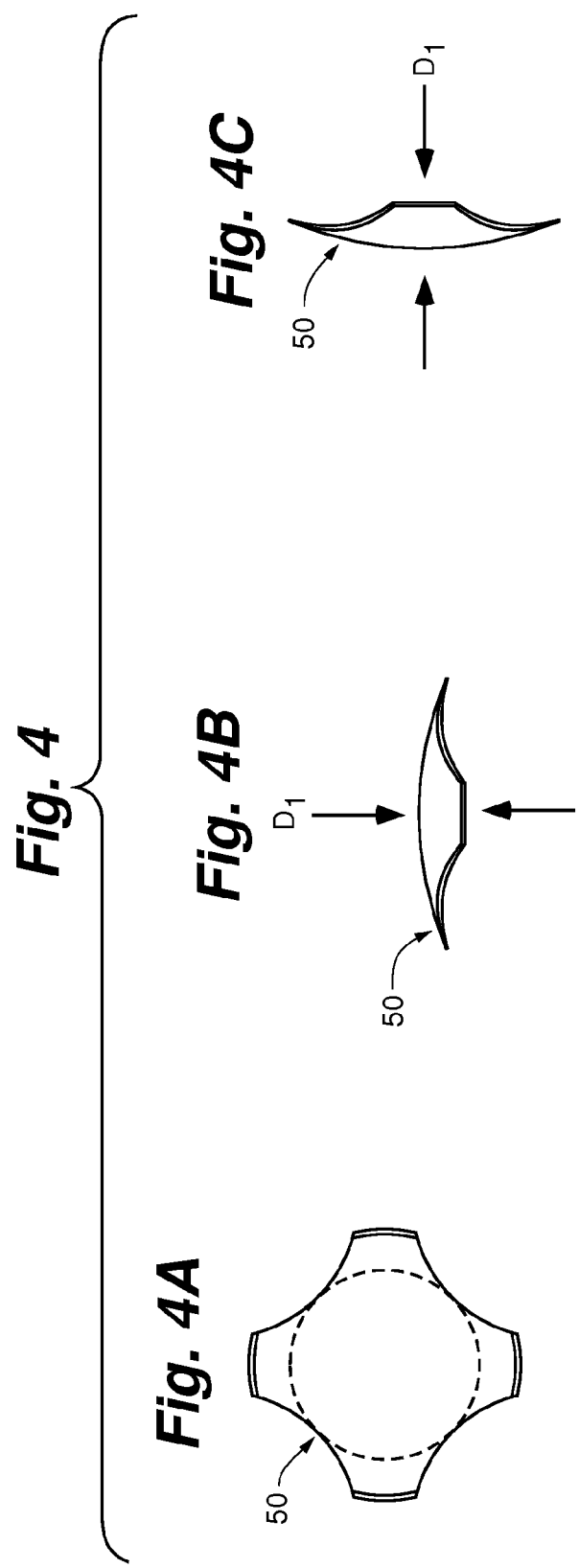

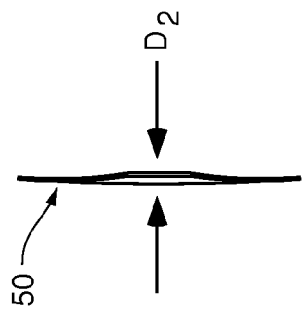
Fig. 5C
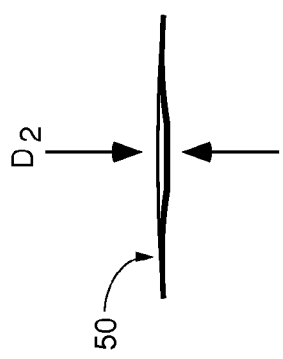
Fig. 5B
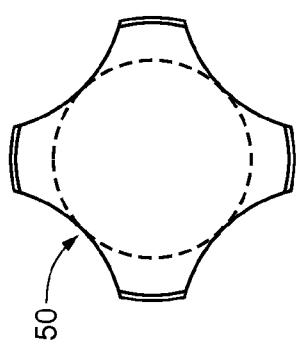
Fig. 5A
Fig. 5

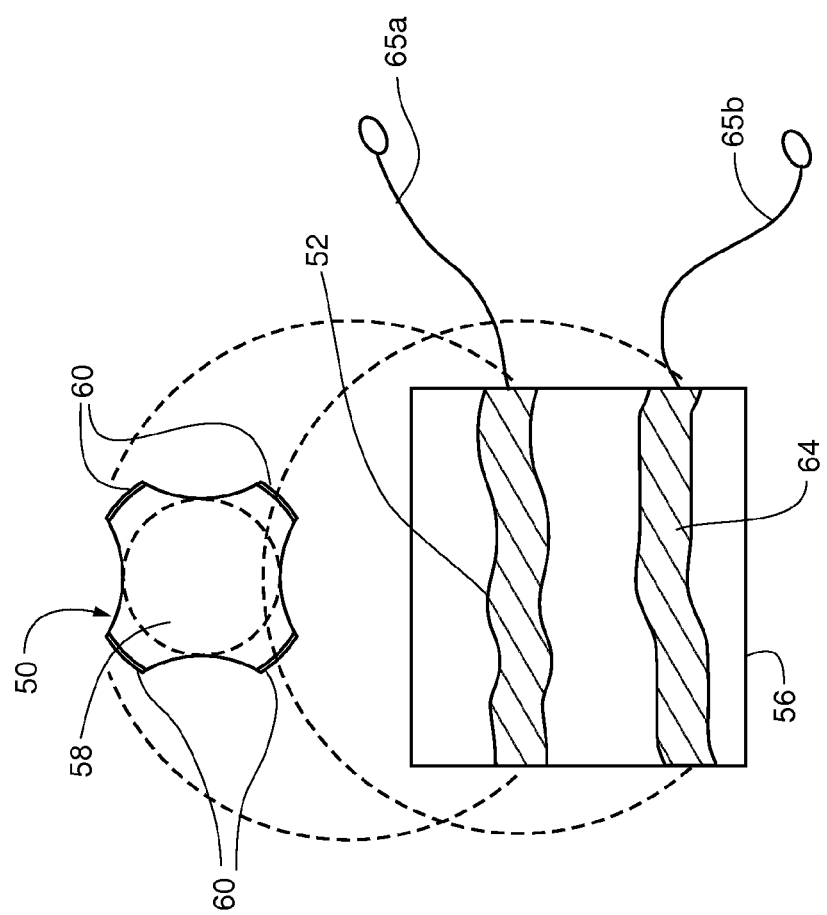

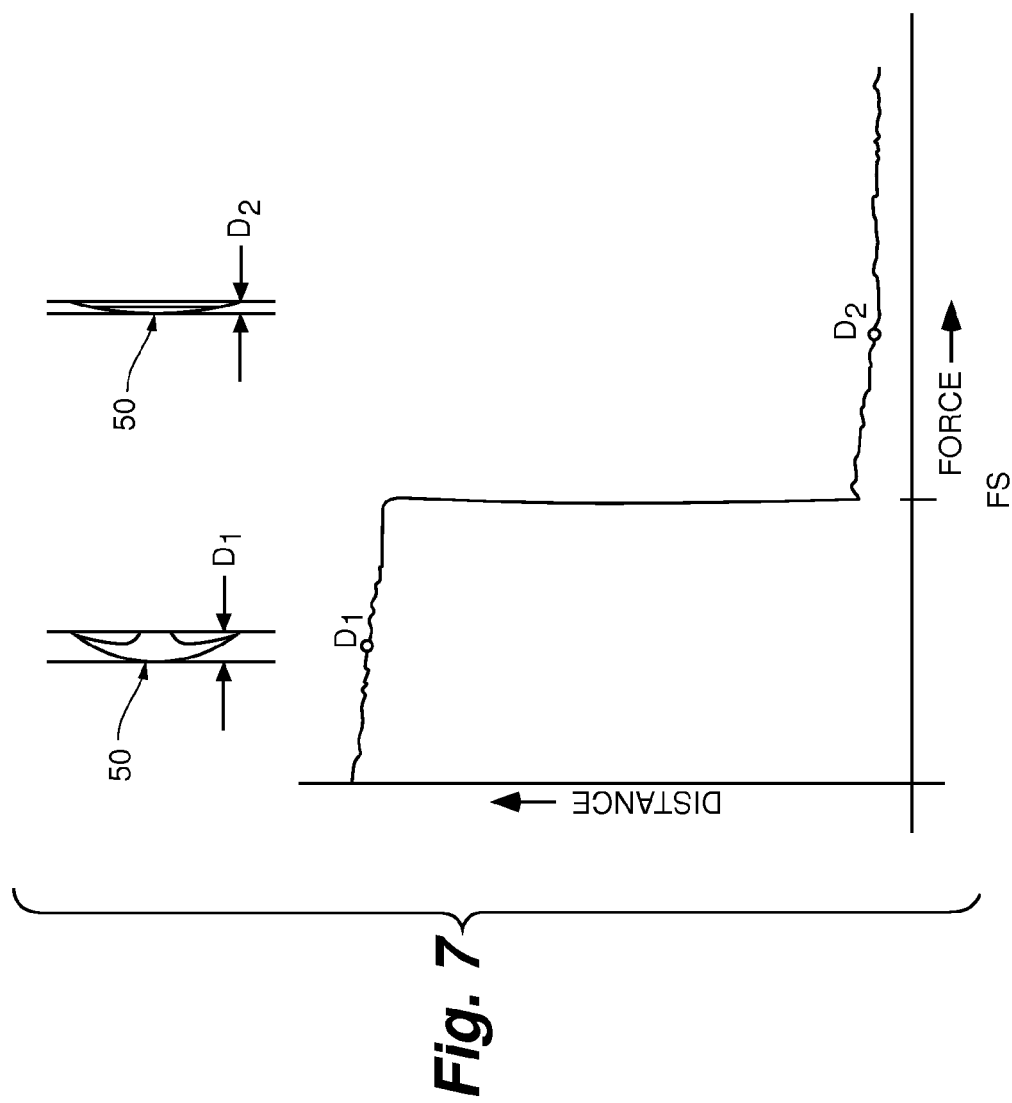

METHOD AND APPARATUS FOR OVERLOAD PROTECTION IN MEDICAMENT SYRINGE PUMPS

CROSS-REFERENCE TO RELATED APPLICATIONS

The present application is a National Phase entry of PCT Application No. PCT/US2015/040739, filed on Jul. 16, 2015, which claims priority to U.S. Provisional Patent Application No. 62/026,942, filed on Jul. 21, 2014, which are hereby fully incorporated herein by reference.

TECHNICAL FIELD

Embodiments relate to medicament infusion pumps. In particular, embodiments relate to a method and apparatus for sensing and protecting against force overloads in driving mechanisms of syringe pumps used to administer medicaments to patients.

BACKGROUND

Syringe pumps are used in a variety of therapy areas to administer drugs, nutritional compositions, and prescribed fluids or fluid-like substances (collectively, "medicaments") to patients in volume and time controlled doses. Medicaments can accurately and continuously be administered by such pumps, at infusion rates typically ranging from as little as 0.1 ml/hr. to as much as 1200 ml/hr. Because of their ability to deliver medicaments in a precise, accurate, and continuous manner, syringe pumps are well suited to pain management and palliative care, for instance, and are also often useful in neonatal and pediatric intensive care units.

In operation, a medicament syringe pump includes a syringe having a plunger that slideably, but tightly, fits inside of a cylinder which in turn contains a medicament. Medicament is administered from the cylinder by operation of the pump in shifting the plunger through the cylinder. Medicament is thus expelled from the cylinder under pressure, through a delivery route comprising a needle, nozzle, tubing, or the like, directing the medicament to a patient. Medicament from a syringe in a syringe pump can be administered, for example, intravenously, intra-arterially, epidurally or subcutaneously. As will be appreciated, a constant and metered application of medicament requires a steady and accurate flow from the syringe in the syringe pump through the delivery route. An unexpected increase in the delivery pressure of the pump can indicate a flow blockage, pump malfunction, or other problem.

A force sensor can be placed in communication with a plunger driver head of a syringe pump, as shown, for example, in U.S. Pat. Nos. 7,635,349 and 6,551,277. A build up of pressure beyond normative operating ranges can accordingly be sensed, triggering alarms and initiating corrective action. Generally, sensors of this type are constructed from either thin foil material or a glass substrate that has been metalized, such as a silicon wafer. Particularly in the case of the latter, rough handling or extreme overloads are of concern, in that the sensor can be irreparably damaged, requiring that the pump be taken out of service for repair.

An overload protection method and system for isolating a force sensor in a syringe pump from the damaging effects of rough handling or extreme overloads, yet still enabling the force sensor to accurately, reliably and repeatedly detect overload conditions and/or provide for overload alarms, would provide decided advantages.

SUMMARY

The problems outlined above are in large measure addressed by embodiments of the apparatus and method for overload protection in medicament syringe pumps. The overload protection apparatus and method hereof provides for normal operation of a medicament syringe pump under normal conditions and expected operating pressures, and provides for the termination of pumping activity, and of the application of pumping force, when normal operating pressures are exceeded. More particularly, a force sensor of the overload protection apparatus and method hereof is physically isolated from overload forces in excess of a set point, and is thereby protected from damage.

The overload protection apparatus and method hereof includes, in an embodiment, a dome switch shiftable between a ready, extended configuration and a collapsed configuration, structure defining a dome switch receptacle for receiving the dome switch, and a plunger stop. The plunger stop is oriented with respect to the dome switch receptacle so as to be engageable with the syringe plunger, or structure operatively coupled to the plunger, of a medicament syringe and syringe pump, and to limit extension of the syringe plunger, or structure operatively coupled to the plunger, into the dome switch receptacle. As used throughout this document the term "dome switch" is intended to include any variable rate spring component or device, or any component or device which tends to collapse with a non-uniform force curve, that is suitable for use in or with embodiments.

BRIEF DESCRIPTION OF THE DRAWINGS

FIG. 3 is similar to FIG. 2, but with the dome switch of the overload protection system in its collapsed configuration in accordance with an embodiment.

FIG. 4a is a plan view of a dome switch used in the overload protection system in accordance with an embodiment, the dome switch depicted in its extended configuration.

FIGS. 4b and 4c are side elevation views of the dome switch depicted in 4a with the dome switch in its extended configuration.

FIGS. 5a, 5b, and 5c are similar to counterpart FIGS. 4a, 4b, and 4c, but with the dome switch depicted in its collapsed configuration.

FIG. 6 is an exploded view depicting a dome switch and dome switch contact plate used in the overload protection system in accordance with an embodiment.

FIG. 7 is a graph depicting the width (distance) of a dome switch used in the overload protection system in accordance with an embodiment as a function of force applied to the dome switch.

DETAILED DESCRIPTION

Figure 1:
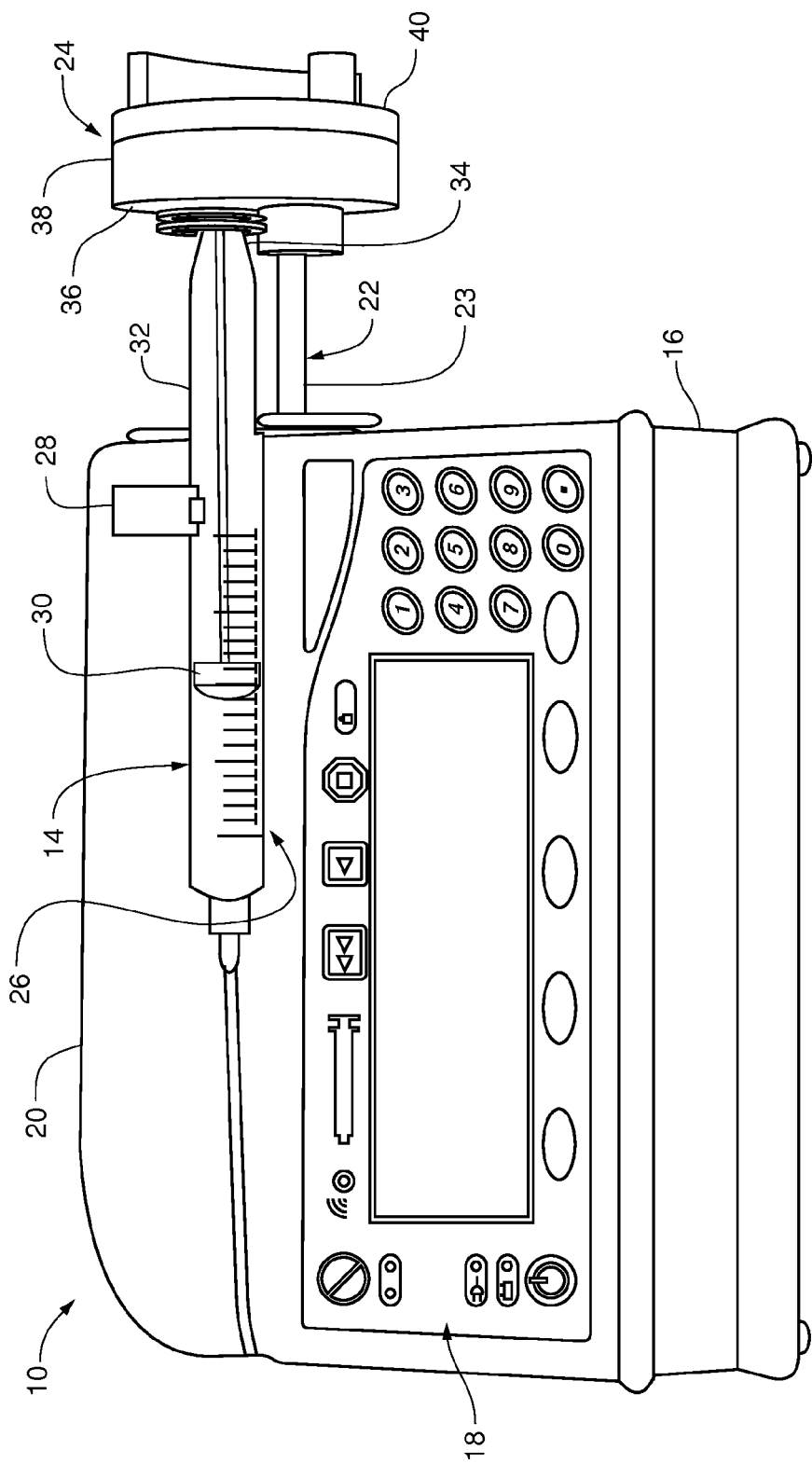
FIG. 1 is a perspective view of a medicament syringe pump having an overload protection system in accordance with an embodiment, with a syringe in place at the top of the pump.

Referring to the drawings, FIG. 1 depicts an example of a medicament syringe pump 10 incorporating an overload protection apparatus 12 in accordance with subject matter hereof. A medicament syringe 14 is depicted in operative position, installed near a top of the syringe pump 10.

Syringe pump 10 includes a base 16, display and user input panel 18, handle 20, and plunger driver 22. Plunger driver 22 includes drive rod 23 and syringe engaging head 24. Syringe 14 is removably received by syringe pump 10 in a syringe cradle 26 formed near a top of syringe pump 10. A syringe clamp 28 acts to retain syringe 14 in place on syringe pump 10. Syringe 14 includes a syringe cylinder 30, and a syringe plunger 32. Syringe plunger 32 includes a thumb press 34 at its distal end. Plunger driver 22 can be activated by an electric drive motor (not shown) of pump 10.

Figure 2:
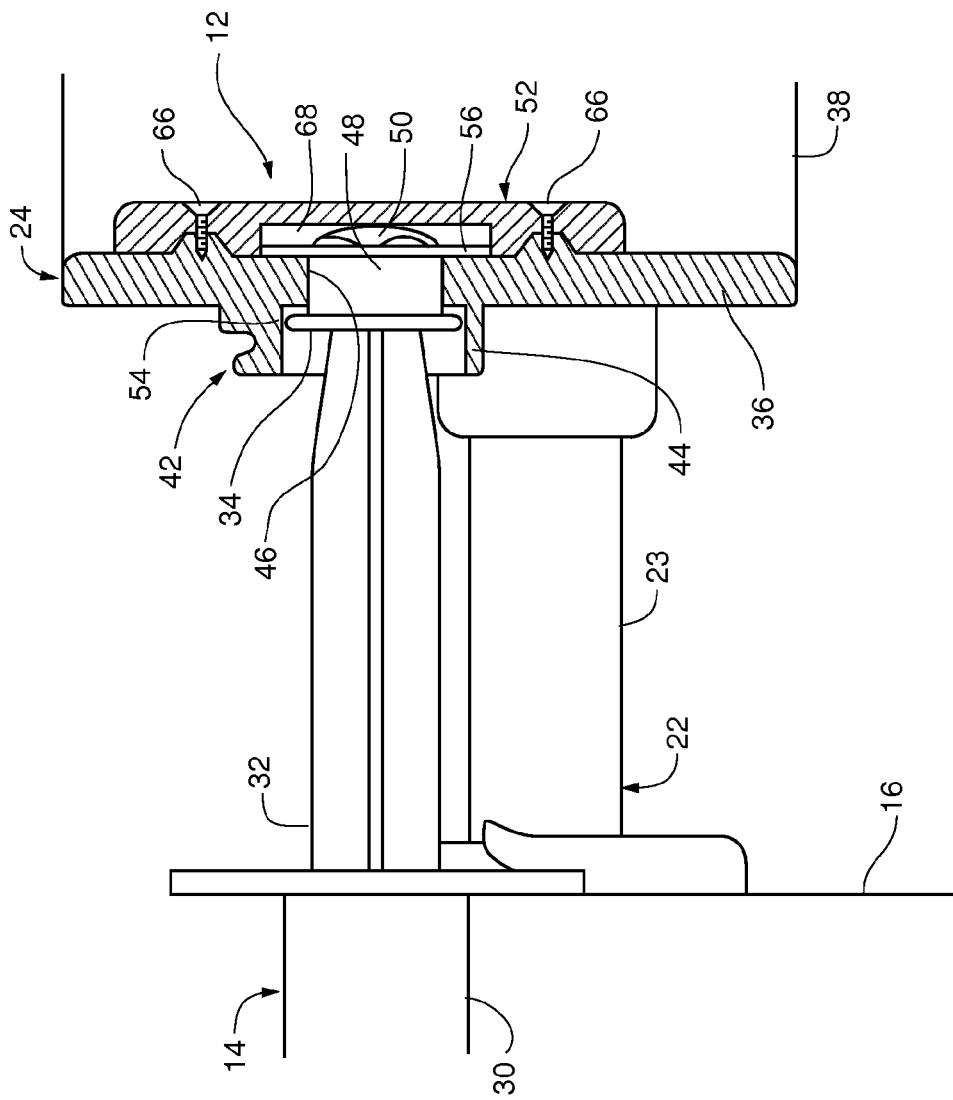
FIG. 2 is a partial, cross sectional view of a medicament syringe pump having an overload protection system in accordance with an embodiment, depicting the thumb press of the syringe operatively engaged by the syringe engaging plunger driver head of the pump.

Referring to FIG. 2, an overload protection apparatus 12 in accordance with an embodiment is depicted mounted on syringe engaging head 24 of plunger driver 22.

Syringe engaging head 24 of plunger driver 22 includes front plate 36, sidewall 38 and back plate 40 (as shown in FIG. 1). Syringe engaging head front plate 36 includes an integral thumb press receptacle 42 defined by sidewall 44, for receiving thumb press 34 of syringe plunger 32. Front plate 36 includes an opening 46 generally aligned (or generally centered) with sidewall 44 of thumb press receptacle 42.

A syringe pump force sensor 48 is received within opening 46 of front plate sidewall 44. Force sensor 48 can be, for instance, a model FX1901 Force Sensor, available from Measurement Specialties, 1000 Lucas Way, Hampton, Va. 23666, www.meas-spec.com. Generally, sensors of this type are constructed from either a thin foil material or a glass substrate that has been metalized, such as a silicon wafer.

Overload protection apparatus 12 includes a dome switch 50, a dome switch retainer 52, and plunger stop 54. A printed circuit board 56 provides electrical connection to dome switch 50. Power to the electric motor (not shown) of pump 10 can be interrupted by operation of dome switch 50, either directly or through a controller (not shown).

Dome switch 50 can be, for instance, a dome switch available from Snaptron, Inc., 960 Diamond Valley Drive, Windsor, Colo. 80550, www.snaptron.com. Dome switch 50 could be of a size of 20.2 mm, with a trip force of 5500 g, for instance. As shown in FIG. 6, dome switch 50 includes a concave/convex switch body 58 and radially extending legs 60. Referring to FIGS. 4a-c and FIGS. 5a-c, a distance along the dome switch longitudinal axis and across the width of dome switch 50 is greater with the dome switch in its extended configuration (FIGS. 4a-c; D1), than the distance across the width of dome switch 50 in its collapsed configuration (FIGS. 5a-c; D2). With reference again to FIG. 6, it will be understood that legs 60 of dome switch 50 can be held against electrical traces 62, 64 on circuit board 56 so as to create an electrical connection between trace leads 65a, 65b, when dome switch 50 is in an extended configuration (FIGS. 4a-c), and that legs 60 are lifted away from electrical traces 62, 64 on circuit board 56 when dome switch 50 is in its collapsed configuration (FIGS. 5a-c), thereby removing the electrical connection. It is to be appreciated and understood that dome switch 50 and its legs 60 represent just one example of variable rate spring components. Thus, any suitable configurations and/or variations of, for example, switch bodies, legs, electrical traces and leads, circuit boards, and electrical connections, could be employed for use in or with subject matter hereof.

In particular, and with reference to the graph of FIG. 7, it will be understood that the distance D1 across the width of a dome switch 50 is relatively constant up to a certain magnitude of force (pressure) applied across the width of dome switch 50. At a critical pressure (Fs), dome 58 of dome switch 50 will collapse (snap), and the distance D2 across the width of dome switch 50 will be at a second, relatively smaller value. Correspondingly, legs 60 of dome switch 50 would respectively transition from being in contact with traces 62, 64 to not being in contact therewith. Although not explicitly shown in FIG. 7, it is to be understood that dome switch 50 at position D1 is under a "pre-load," which may be in some embodiments greater than the working load of the force sensor. It is also to be appreciated that specific embodiments will have specific ranges for D1 and D2, which may vary appreciably among the embodiments.

Dome switch retainer 52 is removably held in place on front plate 36 by screws 66. A cavity 68 is provided on the internal size of dome switch retainer 52, for receiving dome switch 50 and circuit board 56. The depth of cavity 68 is approximately equal to the combined width of circuit board 56 and distance D1 across the width of dome switch 50 when dome switch 50 is in its extended configuration. The depth of cavity 68 is greater, however, than the combined width of circuit board 56 and distance D2 across the width of dome switch 50 when dome switch 50 is in its collapsed configuration.

In operation, and with reference again to FIG. 2, an overload protection apparatus 12 in accordance with embodiments is depicted in place in a medicament syringe pump 10. Syringe engaging head 24 of medicament syringe pump 10 is depicted as being abutably engaged with thumb press 34 of syringe plunger 32. As will be appreciated, leftward motion in FIG. 2 of plunger driver 22 will shift syringe plunger 32 leftwardly, from the perspective of FIG. 2, thus shifting syringe plunger 32 along syringe pump 30, for controllably expelling medicament from syringe 14 in syringe pump 10.

As plunger driver 22 shifts syringe plunger 32 along syringe cylinder 30 to dispense medicament, force sensor 48 will be subject to, and will provide a signal in response to, the drive pressure of plunger driver 22 against syringe plunger 32. As discussed above, if overload pressures are applied to the syringe plunger, either due to blockage, equipment failure, or the like, force sensor 48 will register those pressures, but could be subject to damage when the overload pressures reach a critical limit. It is to be appreciated that overload pressures or forces could also result from other sources such as rough handling or dropping of the pump, or other impacts to the pump or its individual components that are consequently transmitted to the force sensor.

Overload protection apparatus 12 is designed to protect force sensor 48 from damage when overload pressures exceed the critical limit. With reference to FIG. 2, under normal operating pressures, the driving force of plunger driver 22 is transmitted to syringe plunger 32 through syringe engaging head 24, across dome switch 50, circuit board 56, force sensor 48, to thumb press 34 of syringe plunger 32. With reference to FIG. 7, it will be seen that as operating pressure increases up to a critical pressure (Fs), dome switch 50 maintains its extended configuration, and the distance D1 across the width of dome switch 50 remains relatively constant. With reference to FIGS. 7 and 3, when the operating pressure exceeds the critical pressure Fs, dome switch 50 collapses to its collapsed configuration, reducing the distance across the width of the dome from D1 to the smaller D2. As detailed above, the depth of cavity 68 that retains dome switch 50 and circuit board 56 is greater than the combined width of circuit board 56 and the distance D2 across dome switch 50 when dome switch 50 is in the collapsed configuration. Moreover, with reference to FIG. 3, upon collapse of dome switch 50, thumb press 34 engages plunger stop 54 on syringe engaging head 24, arresting the motion of syringe plunger 32 with respect to syringe engaging head 24. Accordingly, dome switch 50 and circuit board 56 become loosely retained in cavity 68, with circuit board 56, and in particular force sensor 48, no longer subject to the (overload) driving force of plunger driver 22, thereby isolating force sensor 48 from damaging, excessive loads. Additionally, in such a state, legs 60 of dome switch 50 are extended away from contact with conductive traces 62, 64 of circuit board 56, interrupting an electrical connection through dome switch 50 between conductive traces 62, 64. The interruption of the electrical connection through dome switch 50 can signal the presence of an overload condition, and initiate pump shut down.

With reference to FIG. 7, the sensitivity of dome switch 50 to an overload force can be increased by pre-loading (i.e., compressing, to some desirable degree) dome switch 50. In particular, selectively reducing the depth of cavity 68 can compress, to some desirable degree, dome switch 50, but still keep the pressure on dome switch 50 lower than the critical pressure (Fs). The additional force to bring the operation pressure up to the critical pressure (Fs) is accordingly less, thereby increasing the sensitivity of overload protection apparatus 12.

Irrespective of a specific embodiment, it is to be appreciated and understood that a method and apparatus for sensing and protecting against force overloads in driving mechanisms of syringe pumps, such as has been described by example or is otherwise contemplated herein, is characterized in that a relative dimension or distance between (i) a surface of a syringe plunger (or structure operatively coupled to the plunger) received in a receptacle of the pump and (ii) the receptacle itself is at all times capable of protecting a sensor in the receptacle from an overload force. Accordingly, selection of individual components of a method and apparatus for sensing and protecting against force overloads in syringe pumps, along with other particulars of composition and construction of an embodiment of such an apparatus and method, may be made as desired in accordance with the novel and inventive subject matter hereof, provided that such particulars of those various embodiments function to protect a sensor in the receptacle from an overload force as aforementioned.

In an embodiment, an overload protection apparatus operatively isolates a syringe pump force sensor from overload forces applied to a syringe that includes a syringe plunger presenting a thumb press. The syringe pump force sensor is operatively couplable to the thumb press for measuring driving forces applied to the thumb press. The overload protection apparatus includes a dome switch presenting a dome switch longitudinal axis and a dome switch width measured along the dome switch longitudinal axis, the dome switch being shiftable between a dome switch extended configuration and a dome switch collapsed configuration, the dome switch presenting a dome switch width being shiftable between a dome switch width extended dimension and a dome switch width collapsed dimension, the dome switch width collapsed dimension being less than the dome switch width extended dimension. The dome switch is operatively engageable with the syringe pump force sensor at a dome switch engaging surface operatively coupled to the thumb press, for transmitting an axial piston driving force to the dome switch and shifting the dome switch between the dome switch extended configuration and the dome switch collapsed configuration. Also, structure defines a dome switch receptacle for receiving the dome switch and orienting the dome switch longitudinal axis generally aligned with the axial piston driving force, the dome switch receptacle presenting a dome switch receptacle end wall and a dome switch receptacle operating depth measurable along the dome switch longitudinal axis between the dome switch receptacle end wall and the dome switch engaging surface when the dome switch is in the dome switch extended configuration Additionally, a plunger stop is operably coupled to the structure defining the dome switch receptacle for operatively engaging the plunger thumb press, and operatively limiting travel of the plunger relative to the structure defining the dome switch receptacle such that the dome switch receptacle operating depth is at all times greater than the dome switch collapsed dimension.

In an embodiment, the dome switch can comprise a variable rate spring device. In an embodiment, the dome switch is configured to collapse with a non-uniform force curve.

In an embodiment, a method of providing overload protection operatively isolates a syringe pump force sensor from overload forces applied to a syringe that includes a syringe plunger presenting a thumb press. The syringe pump force sensor is operatively couplable to the thumb press for measuring driving forces applied to the thumb press. The method comprises providing structure defining a dome switch receptacle for receiving a dome switch, the dome switch presenting a dome switch longitudinal axis and a dome switch width measured along the dome switch longitudinal axis, the dome switch being shiftable between a dome switch extended configuration and a dome switch collapsed configuration, the dome switch presenting a dome switch width being shiftable between a dome switch width extended dimension and a dome switch width collapsed dimension. The dome switch width collapsed dimension is less than the dome switch width extended dimension, and the dome switch is operatively engageable with the syringe pump force sensor at a dome switch engaging surface operatively coupled to the thumb press for transmitting an axial piston driving force to the dome switch and shifting the dome switch between the dome switch extended configuration and the dome switch collapsed configuration, and orienting the dome switch longitudinal axis generally aligned with the axial piston driving force. The method also includes the dome switch receptacle presenting a dome switch receptacle end wall and a dome switch receptacle operating depth measurable along the dome switch longitudinal axis between the dome switch receptacle end wall and the dome switch engaging surface when the dome switch is in the dome switch extended configuration. The method also includes operably coupling a plunger stop to the structure defining the dome switch receptacle for operatively engaging the plunger thumb press, and operatively limiting travel of the plunger relative to the structure defining the dome switch receptacle such that the dome switch receptacle operating depth is at all times greater than the dome switch collapsed dimension.

In an embodiment, the method can further comprise providing the dome switch. In an embodiment, the method can further comprise providing a syringe pump comprising the structure defining a dome switch receptacle and the dome switch.

Various embodiments of systems, devices and methods have been described herein. These embodiments are given only by way of example and are not intended to limit the scope of the overall disclosure or the claims. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the disclosure.

Persons of ordinary skill in the relevant arts will recognize that embodiments may comprise fewer features than illustrated in any individual embodiment described above. The embodiments described herein are not meant to be an exhaustive presentation of the ways in which various features may be combined. Accordingly, the embodiments are not mutually exclusive combinations of features; rather, some embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An overload protection apparatus for operatively isolating a syringe pump force sensor from overload forces applied to a syringe plunger, the syringe plunger presenting a thumb press, the syringe pump force sensor being operatively couplable to the thumb press for measuring driving forces applied to the thumb press, the overload protection apparatus comprising:
 a dome switch presenting a dome switch longitudinal axis and a dome switch width measured along the dome switch longitudinal axis, the dome switch being shiftable between a dome switch extended configuration and a dome switch collapsed configuration, the dome switch presenting a dome switch width being shiftable between a dome switch width extended dimension and a dome switch width collapsed dimension, the dome switch width collapsed dimension being less than the dome switch width extended dimension, the dome switch operatively engageable with the syringe pump force sensor at a dome switch engaging surface operatively coupled to the thumb press for transmitting an axial piston driving force to the dome switch and shifting the dome switch between the dome switch extended configuration and the dome switch collapsed configuration;
 a structure defining a dome switch receptacle for receiving the dome switch and orienting the dome switch longitudinal axis generally aligned with the axial piston driving force, the dome switch receptacle presenting a dome switch receptacle end wall and a dome switch receptacle operating depth measurable along the dome switch longitudinal axis between the dome switch receptacle end wall and the dome switch engaging surface when the dome switch is in the dome switch extended configuration; and
 a plunger stop operably coupled to the structure defining the dome switch receptacle for operatively engaging the plunger thumb press, and operatively limiting travel of the syringe plunger relative to the structure defining the dome switch receptacle such that the dome switch receptacle operating depth is at all times greater than the dome switch collapsed dimension.

2. The apparatus of claim 1, wherein the dome switch comprises a variable rate spring device.

3. The apparatus of claim 1, wherein the dome switch is configured to collapse with a non-uniform force curve.

4. A method of providing overload protection for operatively isolating a syringe pump force sensor from overload forces applied to a syringe plunger, the syringe plunger presenting a thumb press, the syringe pump force sensor being operatively couplable to the thumb press for measuring driving forces applied to the thumb press, the method comprising:
 providing a structure defining a dome switch receptacle for receiving a dome switch, the dome switch presenting a dome switch longitudinal axis and a dome switch width measured along the dome switch longitudinal axis, the dome switch being shiftable between a dome switch extended configuration and a dome switch collapsed configuration, the dome switch presenting a dome switch width being shiftable between a dome switch width extended dimension and a dome switch width collapsed dimension, the dome switch width collapsed dimension being less than the dome switch width extended dimension, the dome switch operatively engageable with the syringe pump force sensor at a dome switch engaging surface operatively coupled to the thumb press for transmitting an axial piston driving force to the dome switch and shifting the dome switch between the dome switch extended configuration and the dome switch collapsed configuration, and orienting the dome switch longitudinal axis generally aligned with the axial piston driving force, the dome switch receptacle presenting a dome switch receptacle end wall and a dome switch receptacle operating depth measurable along the dome switch longitudinal axis between the dome switch receptacle end wall and the dome switch engaging surface when the dome switch is in the dome switch extended configuration; and
 operably coupling a plunger stop to the structure defining the dome switch receptacle for operatively engaging the plunger thumb press, and operatively limiting travel of the syringe plunger relative to the structure defining the dome switch receptacle such that the dome switch receptacle operating depth is at all times greater than the dome switch collapsed dimension.

5. The method of claim 4, further comprising providing the dome switch.

6. The method of claim 4, further comprising providing a syringe pump comprising the structure defining a dome switch receptacle and the dome switch.

* * * * *